United States Patent
Wang

(10) Patent No.: US 9,714,948 B2
(45) Date of Patent: *Jul. 25, 2017

(54) METHOD FOR HIGH-THROUGHPUT PROTEIN DETECTION WITH TWO ANTIBODY MICROARRAYS

(71) Applicant: Yingjian Wang, Holden, MA (US)

(72) Inventor: Yingjian Wang, Holden, MA (US)

( * ) Notice: Subject to any disclaimer, the term of this patent is extended or adjusted under 35 U.S.C. 154(b) by 21 days.

This patent is subject to a terminal disclaimer.

(21) Appl. No.: 14/847,033

(22) Filed: Sep. 8, 2015

(65) Prior Publication Data

US 2017/0067905 A1    Mar. 9, 2017

Related U.S. Application Data

(60) Provisional application No. 62/122,632, filed on Oct. 27, 2014.

(51) Int. Cl.
| | |
|---|---|
| *G01N 33/53* | (2006.01) |
| *G01N 33/68* | (2006.01) |
| *G01N 33/545* | (2006.01) |
| *G01N 33/543* | (2006.01) |

(52) U.S. Cl.
CPC ....... *G01N 33/6845* (2013.01); *G01N 33/545* (2013.01); *G01N 33/54353* (2013.01); *G01N 2440/14* (2013.01)

(58) Field of Classification Search
None
See application file for complete search history.

(56) References Cited

U.S. PATENT DOCUMENTS 7,429,466 B2 *   9/2008   Wang ................ C12Q 1/6837
                                                                     435/40.5
8,709,789 B2 *   4/2014   Wang ............... G01N 27/44739
                                                                     204/450

* cited by examiner

*Primary Examiner* — Jacob Cheu

(57) ABSTRACT

The invention provides a method for detecting one or more biological ligands, where the method generally uses two arrays of biological reagents. The two arrays have two different functionalities: the first array captures the ligands on the array; and the second array delivers detecting reagents to the captured ligands. Use of arrays affords the method high-throughput detection capability; and the use of two different arrays ensures high specificity. The first array has a support structure fixed with a first set of reagents, each at a pre-determined position on the support. The second array has a support structure fixed with a second set of reagents, each at a pre-determined position on the support. The first array contains reagent(s) binding to a ligand, while the second array contains second reagent(s) binding to the same ligand. In preferred embodiments, antibodies are used as reagents, and used in detecting proteins in protein samples.

20 Claims, 5 Drawing Sheets

METHOD FOR HIGH-THROUGHPUT PROTEIN DETECTION WITH TWO ANTIBODY MICROARRAYS

FIELD OF THE INVENTION

The present invention generally relates to methods for detecting a plurality of ligands and more particularly to methods for detecting the expressions, activities and functions of multiple proteins.

BACKGROUND OF THE INVENTION

The availability of a large number of biological reagents, such as hundreds of thousands of cloned DNA sequences, numerous antibodies and recombinant proteins, millions of compounds obtained through combinatory chemical synthesis, has promoted the development of technologies that make use of these reagents in biological research, clinical diagnostics and drug development. Special position-addressable arrays of biological reagents have been designed, in which each of the reagents is placed at a pre-defined position so that it can be identified later by the position. For example, in a DNA array, a large number of cDNA or oligos are immobilized, each at a pre-defined position and can be identified later by that position. DNA arrays are used in large-scale hybridization assays for applications such as monitoring gene expressions (Schena et al., 1995, *Science* 270:467-470; DeRisi et al., 1996, *Nature Genetics* 14:457-460). Arrays of DNA clones in expression vectors are also used to express their encoded proteins in mammalian cells (Ziauddin and Sabatini, 2001, *Nature* 411, 107-110).

In a common type of protein array (capture protein array), many proteins are immobilized on a support, each at a predefined position so that every protein can be identified subsequently by its unique position. Capture protein arrays are used to capture ligands onto the array support for subsequent analysis. Two types of capture protein arrays are widely used: antibody arrays and recombinant protein arrays, which contain a plurality of antibodies and recombinant proteins, respectively. Antibody arrays are particularly useful in revealing protein expressions and activities: it is possible to use them to study the properties of a large number of cellular proteins in a single assay. Antibody arrays have been applied in studying in vivo protein-protein interactions, protein posttranslational modifications and protein expression patterns (U.S. Pat. No. 6,197,599).

In another type of protein arrays, dissociable protein arrays, proteins are immobilized on a support in such a way that the immobilized proteins can dissociate from the array support when placed in contact with their interacting ligands that are immobilized on another support (Wang, "Immunostaining with dissociable antibody microarrays". Proteomics 4, 20-26. 2004). Dissociable protein arrays are used to deliver a plurality of reagents to their binding ligands in a position-addressable manner. They have been used in detecting protein expressions and subcellular localizations (Song et al. 2008 "Protein Expression Profiling of Breast Cancer Cells by Dissociable Antibody Microarray (DAMA) Staining". Molecular & Cellular Proteomics 7:163-169. Fu et al. 2010 Protein Subcellular Localization Profiling of Breast Cancer Cells by Dissociable Antibody MicroArray (DAMA) Staining. Proteomics. 10(8):1536-44).

In addition, arrays of cells, tissues, lipids, polymers, drugs and other chemical substances can be fabricated for large scale screening assays in medical diagnostics, drug discovery, molecular biology, immunology and toxicology (Kononen, et al., Nature Medicine, 4:844-7, 1998).

Proteins are the major component of cells and they play important roles in various cellular processes. The entire human genome contains 20,000 to 25,000 protein-encoding genes. Although a given cell may contain the DNA encoding all the proteins, it usually only expresses a fraction of them. A cell line usually expresses about 10,000 proteins and a tissue may express an even higher number of proteins. The protein expression pattern of a cell determines its shape and function; and abnormal protein expressions cause cells to malfunction, resulting in diseases. Therefore, one major task of proteomics is to identify the protein expression patterns in a given source.

A protein with an identical primary amino acid sequence may be present in different forms in the cells largely due to posttranslational modifications. Since in many cases only special posttranslationally modified proteins are activated and directly involved in a cellular process, the detection of these activated proteins in the cells can provide valuable information on that cellular process. There are many types of protein posttranslational modifications including phosphorylation, glycosylation, and ubiquitination. And they play important roles in regulating protein activities. Phosphorylation in either serine, threonine or tyrosine residues is an important mechanism in signal transduction. Aberrant protein phosphorylation contributes to many human diseases. Among the methods of detecting protein phosphorylations, metabolic labeling of cells with radioisotopes and immuno-detection with antibodies against phosphoproteins are most commonly used. However, these methods are usually only applicable to the analysis of one or a few proteins at a time. Although antibodies specific for phosphorylated amino acids, such as PY20 and 4G10, can reveal multiple phosphorylated proteins, they alone are unable to identify individual phosphorylated proteins. New methods for simultaneously detecting the presence of multiple phosphorylated proteins or other modified proteins are highly desirable for signal transduction studies and clinical diagnosis.

Quantification of protein expressions has applications in a variety of fields including biomedical research, disease diagnosis, identification of therapeutic targets, and profiling cellular responses to toxins and pharmaceuticals. In basic biomedical research, it is usually desirable to know what proteins are expressed in specific cells or under specific conditions. And by comparing the protein expression profiles between different cell types, it is possible to identify those proteins whose expressions and activations characterize a particular cell type. In many signal transduction pathways, certain proteins are specifically activated; and the detection of these active proteins, e.g., phosphorylated proteins, may provide important information on the activations of specific signal transduction pathways.

Many diseases alter protein expressions and in many cases abnormal protein expressions are the causes of the diseases. Therefore, determination of protein expression profiles and comparison of the expression profiles between normal and abnormal biological samples are useful for understanding disease mechanisms. Detecting proteins is also useful in clinical diagnostics. For example, examination of the presence of several viral proteins instead of just one in a blood sample is a more reliable diagnostic method for viral infections. Profiling proteins will be invaluable in distinguishing normal cells from early-stage cancers and also from malignant, metastatic cancer cells that are the real killers. In addition, proteins are the targets of most drugs, and protein expression profiling is useful in key areas of drug development, such as in drug target selection, toxicology and the identification of surrogate markers of drug response.

It has long been the goal of molecular biologists to develop technologies that can quantify, in a reliable and reproducible manner, the expression level of every individual protein and the different forms of each protein in a biological sample. However, this has turned out to be extremely difficult to achieve. Traditionally, the expression of one or a small number of proteins can be detected by immunological methods, such as western blotting and Enzyme-Linked Immunosorbent Assay (ELISA).

Immunochemical staining is a versatile technique in determining both the presence and localization of an antigen (Harlow and Lane, Antibodies, a laboratory manual, Cold Spring Harbor Press, 1988). Two-dimensional gel electrophoresis can be used to analyze the proteins expressed in a sample. However, it requires complicated procedures and it is necessary to determine the identities of the proteins displayed on the two-dimensional gel, which is difficult to achieve for most proteins. Recently, protein arrays are applied in studying protein expression patterns. In one strategy (U.S. Pat. No. 6,197,599; Haab, et al., *Genome Biol.* 2, research 0004.1-0004.13, 2001), an antibody array is incubated with a protein sample and after incubation and washing, proteins specifically bound to their respective antibodies on the array are detected. The most challenging problem of the current protein array technology is low specificity. The problem is due primarily to the so-called "non-specific" binding of capture and detection reagents (e.g. antibodies). "Cross-talk" between those reagents creates false signals in protein array methods.

SUMMARY OF THE INVENTION

It is an object of the invention to provide methods that enable one to detect proteins and their properties, and more particularly, to detect and compare the presences of proteins in biological samples. The methods of the invention are designed to substantially improve the quality of protein detection assays. For example, two arrays of antibodies immobilized on two solid supports are used in the methods so that two antibodies are employed to detect one antigen while avoiding the interference from other antibodies on the arrays.

The method may include steps of providing a ligand array on a first support on which two or more ligands are immobilized, each at one or more predefined positions; providing a dissociable reagent array, comprising a second support on which two or more dissociable reagents are immobilized, each at one or more predefined positions; aligning and contacting the ligand array with the dissociable reagent array whereby the dissociable reagents bind to one or more of the ligands on the first support; separating the second support from the first support; and detecting the dissociable reagents bound to the ligands on the first support, whereby two or more ligands are detected.

In another preferred embodiment, the method generally includes the steps of providing a capture reagent array comprising a first support immobilized with one or more capture reagents, providing a dissociable reagent array comprising a second support immobilized with one or more detection reagents, contacting the capture reagent array with a ligand mixture whereby one or more members of the capture reagents bind to the ligands, and capture the ligands onto the first support; contact the dissociable reagent array with the ligands captured onto the capture reagent array; separating the dissociable reagent array from the capture reagent array; detecting the detection reagents that dissociated from the dissociable reagent array and bound to the ligands captured on the capture reagent array.

In the method, after the capture of ligands onto the first support, the capture reagents and the captured ligands may be covalently cross-linked so that the ligands stays on the first support during subsequent process. Cross-linkers such as aldehydes (formaldehyde and glutaldehyde) are preferred.

In another preferred embodiment, the method generally includes the steps of providing a first support on which a set of one or more capture reagents are immobilized to make a capture reagent array; incubating the capture reagent array with a ligand mixture whereby a plurality of the reagents bind to the ligands, and capture the ligands onto the first support; providing a second support and contacting the capture reagent array with the second support; transferring and immobilizing the ligands captured by the capture regents to the second support; providing a third support on which a set of detection reagents are immobilized to make a dissociable reagent array; align and contact the second support and the dissociable reagent array support whereby the detection reagents on the dissociable reagent array bind respective interacting ligands on the second support; separating the second support from the third support, whereby, one or more of the detection reagents remain bound to the ligands on the second support; detecting the detection reagents dissociated from the dissociable reagent array and bound on the second support.

Another preferred method of the invention for detecting one or more ligands comprises the steps of immobilizing a set of one or more capture reagents on a first support to make a capture reagent array; immobilizing a set of one or more detection reagents on a second support to make a dissociable reagent array; contacting said capture reagent array with a mixture of ligands to allow one or more members of said first set of reagents to bind with one or more of said ligands; aligning and contacting the dissociable reagent array with the capture reagent array, whereby some of the detection reagents bind to the ligands; separating the second support from the first support to allow one or more of said detection reagents that are bound to one or more of the ligands to dissociate from the second support; contacting the first support containing captured ligands and their interacting detection reagents with a third support; and transfer the detection reagents to the third support; separating the first support from the third support; detecting one or more of the detection reagents on the third support.

In the methods, after the binding between capture reagents and ligands, or between ligands and detection reagents; the complexes may be covalently cross-linked so that the complexes stay together during subsequent process.

In the method of the present invention, reagents and ligands are immobilized at one or more predetermined positions on the supports. If the reagent selected is one or more antibodies, the antibodies may be specific for post-translationally modified proteins such as phosphorylated proteins. The number of different kinds of reagents that can be immobilized on a support may be 5 to 100,000; 200 to 10,000; 20 to 1,000; and 5 to 500. The supports may comprise materials selected from a group consisting of nitrocellulose, nylon, polyvinylidene difluordie, glass, or plastic, and their derivatives. Proteins such as antibodies may be immobilized on the supports in one or more shapes selected from a group consisting of circular, elongated, and polygonal.

DESCRIPTION OF THE PREFERRED EMBODIMENTS AND METHODS

Figure 1:
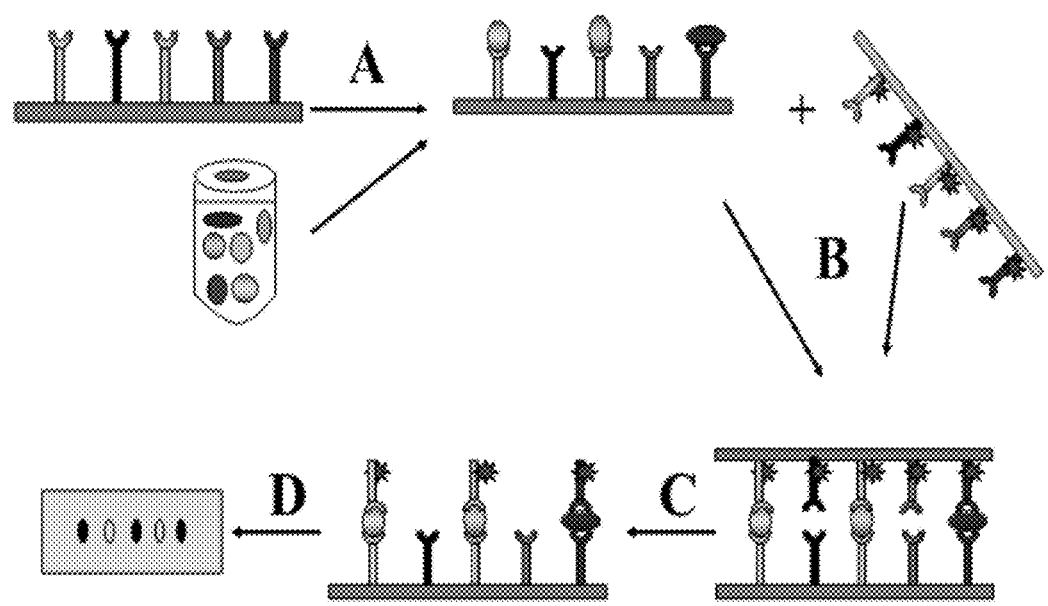
FIG. 1 is a schematic diagram of a preferred method of the invention for detecting multiple proteins using two antibody arrays.

The invention relates to detection methods using arrays of biological reagents. The method generally includes the steps of providing a capture reagent array comprising a first support immobilized with one or more capture reagents, providing a mixture of ligands to be detected, providing a dissociable reagent array comprising a second support immobilized with one or more dissociable reagents, contacting the capture reagent array with the mixture of ligands whereby a plurality of the capture reagents bind to the ligands, and capture the ligands onto the capture reagent array support. The method may further comprise the steps of contacting the dissociable reagent array with the capture reagent array whereby each of the dissociable regent make contact with their interacting ligands captured on the capture reagent array, separating the dissociable reagent array from the capture reagent array, and detecting one of more dissociable reagent that dissociated from the dissociable reagent array and remain bound on the capture array.

The term "reagents" as used herein refers to any molecules of biological interest, such as antibodies, recombinant proteins, synthesized peptides, DNA, RNA, nucleotides, and small chemicals.

The term "ligands" as used herein refers to any biological molecule that is interactive with one or more reagents. Ligands are usually present in a biological sample, such as serum, cells, tissues or their lysates. Ligands can be proteins, antigens, etc. A ligand may have several properties that are of interest. For example, the properties of a protein may refer to its expression level in a protein sample, its interaction with another protein, its phosphorylation/activation state etc. Ligands may be present in a protein sample. The term "protein sample" as used herein refers to a protein mixture. For example, it can be a lysate from a cell line or tissue. A protein sample can be from various sources such as, but not limited to, cultured cell lines, human or animal tissue, or blood. In a preferred embodiment, protein samples are blood from human or animal. In another embodiment, serum and serum devoid of certain components such as albumin are used as protein samples. In another preferred embodiment, protein samples are protein lysates prepared from cells or tissues by lysis. A typical lysis buffer contains detergents such as sodium dodecyl sulphate (SDS), Triton X-100, etc.

The term "support" is used herein, for the purposes of the specification and claims, to mean the structure on which reagents or ligands are directly deposited and immobilized. The support and the immobilized reagents usually form covalent or non-covalent bonds. In practice a support is usually a well-less structure, in the form of a flat surface of a membrane or a slide, with thickness of less than 10 mm. It is different from devices such as test tubes and 96-well plates that hold a liquid within the device. In the preferred embodiments, the supports may be, but are not limited to, rigid plates or membranes made of glass, plastics, nitrocellulose, nylon, polyvinylidene difluoride (PVDF), or their derivatives. Membranes are easier to handle and reagents/ligands can be readily immobilized on them. Glass or plastic plates provide rigid support and are necessary in some applications. In a preferred embodiment, a support is polymer-coated glass or plastic plate. Polymer may be nitrocellulose and nylon, etc. Nitrocellulose-coated glass slides are commonly used and commercially available (for an example, FAST slides from Maine Manufacturing).

The term "immobilization" is used herein, means the restriction of a reagent or a ligand on a support so that the movement of the reagent or ligand on the support is limited. For example, when an antibody is immobilized on a support, the antibody is attached to the support so that it may not dissociate from the support and the movement of the antibody on the support is also limited. However, under some conditions, as described in the invention, an immobilized reagent can dissociate from the support. The physical and chemical nature of the immobilization determines whether an immobilized reagent can dissociate from the support; and how efficient the dissociation will be.

Preferably, the solid supports are pretreated so that biological reagents deposited on them can be immobilized with adequate strength suitable for specific applications. One way to treat the solid support is to coat the solid supports with a layer of polymers that in turn will interact with biological reagents through non-specific, non-covalent bonds. For example, polymers comprising polylysine or polyethyleneimine may be used to coat glass slides or coverslips for use in immobilizing biological molecules.

Several techniques are available for depositing and immobilizing a plurality of biological reagents on solid supports, such as those described by Lehrach, et al. (Hybridization fingerprinting in genome mapping and sequencing, genome analysis, Vol. 1, Davies and Tilgham, Eds, Cold Spring Harbor Press, pp. 39-81, 1990) and Brown et al. (U.S. Pat. No. 5,807,522). Each of the aforementioned articles is incorporated by reference in its entirety. For example, nano-litre volumes of antibodies in an aqueous solution can be printed on a glass slide using a robotic arrayer. Therefore, arrays of biological reagents may be formed by depositing a plurality of reagents onto a flat solid support, one or a few reagents at a time, and each reagent at a pre-defined position.

The immobilization of reagents may be via adsorption (Trevan, 1980, Immobilized Enzymes: an introduction and their application in biotechnology. Wiley, Chichester). The adsorption forces involved may be nonspecific, hydrophobic or ionic interactions. Typical adsorbent materials include, but are not limited to, clay, charcoal, hydroxyapatite, and most frequently, ion-exchange materials such as DEAE-Sephadex.

Entrapment is another way to immobilize reagents (Trevan, 1980, Immobilized Enzymes: an introduction and their application in biotechnology. Wiley, Chichester). The entrapped antibodies are not attached to the polymer; their free diffusion is merely restrained. One commonly used matrix is a polyacrylamide gel. In one preferred embodiment, capillary tubes are used to facilitate arraying and immobilizing biological reagents. The capillary tubes may be made from materials such as plastics and glass, which preferably do not interfere with the properties of biological reagents. The heights of the capillary tubes may be varied from micrometers to meters. A biological reagent is usually filled into a capillary tube as liquid solution. After filling, the reagent solution becomes solidified and the reagent is immobilized. The strength of immobilization may be varied depending on a given application.

Reagents are immobilized on a solid support directly or indirectly. For example, reagents may be directly deposited at high density on a support, which can be as small as a microscopic slide. Similar technology was developed for making high density DNA microarray (Shalon et al., Genome Research, 1996 July; 6(7): 639-645). Reagents may also be immobilized indirectly on the support. For instance, protein A or protein G, or their mutants can be first printed on a support as intermediates. Antibodies are then immobilized on the support through their interactions with protein A or G. One advantage of this method is that, by engaging the constant regions of antibodies with protein A or G, the variable regions of the antibodies (antigen-binding domains) will be fully exposed and available to bind antigens. Another advantage is that, since protein A or G can be modified to change their binding affinity for antibodies, when carefully designed mutants of protein A or protein G are used, antibodies can be immobilized on the support with desired strength. As such, antibodies on one hand can be immobilized on the support without losing positional information but on the other hand can leave the support and bind to other ligands of higher affinity. Recombinant fusion proteins can be immobilized through the interactions between their tags and the ligands attached on the support. For example, intermediates (e.g., glutathione or nickel) can be first covalently attached on a support and then recombinant fusion proteins containing a tag (e.g., GST or 6xHis) are immobilized on the same support via interacting with the ligands. The tags and ligands can be modified to change their affinities so that the immobilization will have desired strength.

The term "array", as used herein refers to a device that includes, but is not limited to, a solid support and a plurality of reagents or ligands immobilized on the support, each at a predefined position. "Ligand array" as used herein refers to a device that comprises a solid support on which ligands are immobilized at two or more positions. "Reagent array" as used herein refers to a device that comprises a solid support on which reagents are immobilized at two or more positions.

For example, a plurality of antibodies may be immobilized on a support to make an antibody array, each antibody at a predefined position so that each it can be identified by a specific position on the support. Array support can be a support as described above. Reagents such as antibodies are usually deposited on an array support as circular dots. However, antibodies can also be deposited in other shapes. For example, antibodies can be immobilized in an elongated shape, such as a rectangular shape of a few microns to a few centimeters wide and a few microns to a few centimeters long. The distance between neighboring reagent spots (array pitch) can range from a few microns to a few millimeters. Generally microarrays refer to arrays with a pitch less than a few hundred microns. For the purpose of description, Arrays and microarrays are used herein interchangeably.

In the present invention, different types of reagent arrays are used. The term "capture reagent array", as used herein refers to a reagent array that is used to bind and capture ligands on the reagent support. The support may comprise materials selected from a group consisting of nitrocellulose, nylon, polyvinylidene difluordie, glass, or plastic, and their derivatives. In a preferred embodiment, the support comprises nitrocellulose. In another embodiment, the support comprises glass. One type of capture reagent array is capture antibody array that is used herein to refer to an antibody array that is used to bind and capture ligands on the antibody array support. The antibodies on a capture antibody array may be from the same species (e.g. mouse, rabbit, goat, etc), or from different species. In a preferred embodiment, all antibodies are mouse antibodies. In another preferred embodiment, all antibodies are rabbit antibodies.

"Capture reagent", as used herein refers to reagents that are immobilized on a capture reagent array. "Capture antibody", as used herein refers to antibodies that are immobilized on a capture antibody array. The reagents may be immobilized at one or more predetermined positions on said first support. If the reagents are antibodies, antibodies may be specific for posttranslationally modified proteins such as phosphorylated proteins. One or more of the capture reagents may be each immobilized at one or more predetermined positions on the capture reagent array. The number of different kinds of reagents on any given array is preferably from 5 to 100,000; from 200 to 10,000; from 20 to 1,000; from 5 to 500; from 5 to 100; and from 5 to 50.

The term "dissociable reagent array" as used herein refers to a reagent array that one or more reagents are immobilized on an array support in such a manner that when they make contact with ligands that are fixed on another support, the reagents can bind to their respective target ligand. And when the array support is separated from the support on which ligands are fixed, the reagents will dissociate from the array support and remain bound to the ligands on the support.

"Dissociable reagent" as used herein refers to a reagent that is immobilized on a dissociable reagent array. "Dissociable antibody" as used herein refers an antibody that is immobilized on a dissociable antibody array. "Detection reagent" is also used to refer the reagent immobilized on a dissociable reagent array. In the methods of the present invention, at least part of each dissociable reagent/antibody usually dissociates from array support and transferred to another support, such as a ligand support or a capture array support. The detection reagents may be immobilized at one or more predetermined positions on a dissociable array support. If the reagents are antibodies, antibodies may be specific for posttranslationally modified proteins such as phosphorylated proteins. The number of different kinds of detection reagents on any given dissociable array is preferably from 5 to 100,000; from 200 to 10,000; from 20 to 1,000; from 5 to 500; from 5 to 100; and from 5 to 50.

In a preferred embodiment, a ligand array is used with a dissociable reagent array to detect the properties of two or more ligands. For example, biological sample(s) containing two or more ligands can be immobilized on a first support to make a ligand array. Then the ligand array is aligned and contacted with a dissociable reagent array on a second support. During the contact period, the reagents bind to the ligands. Then the dissociable reagent array is removed from the ligand array support. The reagents bound to the ligands will dissociate from the second support and transferred to the first support. By detecting the reagents on the first support the properties of the ligands, such as their abundance in the biological sample can be revealed. The number of different kinds of ligands on a ligand array is preferably from 5 to 100,000; from 200 to 10,000; from 20 to 1,000; from 5 to 500; from 5 to 100; and from 5 to 50.

A ligand array can be made by using a capture reagent array. In a preferred embodiment, a first reagent array (capture reagent array) on a first support is incubated with a mixture of ligands; some ligands are captured and separated by respective capture reagents immobilized on the first reagent array, thus effectively creating a ligand array on the first support. After removing non-binding ligands, the ligands captured on the first reagent array is aligned and contacted with their respective dissociable reagents on a second reagent array (dissociable reagent array) on a second support, whereby the dissociable reagents binds the ligands. When the second reagent array is removed from the first reagent array, the ligand-bound dissociable reagents dissociate from the second reagent array support and transferred to the first reagent array support. A capture reagent on the first reagent array and a dissociable reagent on the second array bind to the same ligand and they may be immobilized at corresponding positions.

In the method, the dissociable reagent array needs to be aligned with the capture reagent array so that each dissociable reagent makes contact with its interacting ligand that captured by the capture reagent. The alignment can be achieved either manually or automatically. In a preferred embodiment, the capture reagent array and the dissociable reagent array have exactly the same shape, size, and the capture reagent and the dissociable reagent interacting with the same ligand are at the same position on the respective array; therefore, when the two arrays are placed together with the edges aligned, the reagents will be aligned as well. Other alignment methods known to the person familiar with the art may also be used.

The dissociable reagents that dissociate from the second reagent array support and bind to the ligands on the first reagent array support can be detected by known arts. In one approach, the dissociable reagents are labeled with a tag (e.g. biotin or fluorescent molecule) and they are detected via the tag. Another common method is to use enzyme-conjugated secondary antibodies, such as horseradish peroxidase or alkaline phosphatase conjugated goat anti-rabbit and goat anti-mouse antibodies. Fluorescent-labeled secondary antibodies can also be used. Other technologies that can be used include immuno-PCR (Sano et al., 1992, *Science* 258, 120-122), rolling circle DNA amplification technique (Schweitzer et al., 2000, *Proc. Natl. Acad. Sci. USA* 97, 10113-10119), and immuno-detection amplified by T7 RNA polymerase (Zhang et al., 2001, *Proc. Natl. Acad. Sci. USA, Vol.* 98, 5497-5502). When antibodies are used as both capture reagents and dissociable reagents, they can be from the same or different species. In one preferred embodiment, all antibodies on the first antibody array are from rabbits while all antibodies on the second antibody array are from mouse. In another preferred embodiment, all antibodies on the first antibody array are from mouse while all antibodies on the second antibody array are from rabbit.

The methods of the present invention have significant advantages over other methods. In the method, two antibody arrays (one capture antibody array and one dissociable antibody array) are used for detecting ligands. Comparing with the method of using just one capture or just one dissociable antibody arrays, the present method is more specific. In the present method, each ligand is first "purified" by the capture antibodies. Therefore, each detection antibody (on the dissociable antibody array) binds to its targets in the presence of much less other proteins, thus the non-specific binding is minimized.

Besides the usual advantages that protein array method can offer (high throughput, less reagents and protein samples required, etc.) the present method has several advantages over previous capture antibody array method. First, the present method has higher specificity than the capture array method. It has higher specificity than the label-based antibody array method because the present method uses two antibodies for each target while the label-based antibody array method uses one antibody for each target. It also has higher specificity than the sandwiched antibody array method because although the sandwiched array method uses two antibodies for each target it suffers from the problem of cross-talk. In contrast, the present method eliminates the problem of cross-talk by using immobilized dissociable antibodies as detection antibodies. Second, the present method has increased sensitivity. With increased specificity and the use of detection antibodies, the method can use signal amplification in detection and thus have increased sensitivity. Third, the present method has higher throughput than the multiplex sandwiched microarray method. The problem of cross-talk limits the number of antibodies that can be used in the detection mixture in the sandwiched method. Experience puts the limit at around 50 antibodies. By avoiding cross-talk, the present method can use any number of antibodies on an array. Therefore, the number of protein targets that can be analyzed by present method in each assay is much expanded. Fourth, although the present method requires a capture antibody microarray and a dissociable microarray, because of the lack of cross-talk and increased specificity, it would be easier to obtain satisfactory antibody pairs for the present method than that for previous sandwiched microarray method. In additions, because two antibodies are used for the recognition of an antigen, antibodies with off-target binding can be used. Thus the pool of usable antibodies is much expanded.

In another preferred embodiment, a protein sample containing the target ligands is first incubated with a capture antibody array on a first support to allow capture antibodies to capture their interacting ligands/antigens on the array. Non-binding proteins can be washed off. The proteins/ligands captured at each position are dissociated from the capture antibodies (therefore, the capture antibody array) and transferred onto a second support (ligand support) and immobilized on it. The interactions between the capture antibodies and the capture antibody array support can be stronger than the interactions between the capture antibodies and the ligands/antigens. Therefore, conditions may be found to disrupt antibody-antigen interactions but leave antibody immobilization on the first support intact. Under such conditions, the ligands/antigens but not the capture antibodies may be transferred onto the second support and immobilized on it. To avoid the dissociation of capture antibodies from the array supports, the antibodies may be covalently immobilized on the supports. After transfer, the second support containing the transferred ligands/antigens is then contacted with a dissociable antibody array on a third support, whereby one or more dissociable antibodies on the third support bind to the ligands/antigens on the second support. When the dissociable antibody array is separated from the second support; some dissociable antibodies dissociate from the third support and remain bound to the ligands/antigens on the second support. The amount of dissociable antibody transferred to the second support will be proportional to the abundance of its antigens in the ligand mixture. Therefore, the detection of the amount of dissociable antibodies on the second support will reveal the abundance of their antigens in the protein sample.

In a typical transfer of captured ligands to a second support, the capture antibody array containing the captured ligands is placed in contact with the second support. Then they are placed in a buffer solution that could disrupt the interactions between the ligands/antigens and the capture antibodies. In a preferred embodiment, an electric current is applied to promote the transfer of dissociated proteins from the first support to the second support. After completion, the two supports are separated. The transfer and immobilization may happen simultaneously or can be done sequentially. That is, proteins are transferred first and then immobilized. If the immobilization is not as strong as required, it can be reinforced, e.g., through covalent bonds.

Transfer of ligands to a third support has advantages in practice. For example, if capture and dissociable antibodies from the same animal sources are used; after ligand transfer, secondary antibodies can still be used in detecting dissociable antibodies without the interference of the capture antibodies.

In another preferred embodiment, a ligand mixture (protein sample) is first incubated with a capture antibody array to allow antibodies to capture their respective interacting ligands on the array. Non-binding proteins can be washed off. The ligand-bound capture antibody array is then contacted with a dissociable antibody array. The two arrays are aligned so that the dissociable antibodies on the dissociable antibody array can bind to their respective interacting ligands captured on the capture antibody array. After incubation, the dissociable antibody array is removed from the capture antibody array; dissociable antibodies bound to the ligands will dissociate from the dissociate antibody array and remain bound to the ligands on the capture antibody array. The capture antibody array containing the captured ligands and the binding dissociable antibodies is then contacted with a third support. Conditions are applied to dissociate the dissociable antibodies from the capture antibody array and transfer, immobilize them on the third support. The transfer is preferred done in such a way that the transferred reagents or ligands retain their relative positions so that they can be identified on the support. The transferred dissociable antibodies on the third support are then detected, e.g. with fluorescent secondary antibodies.

Transfer of dissociable antibodies to a third support has advantages in practice. For example, if capture and dissociable antibodies from the same animal sources are used; after transfer, secondary antibodies can still be used in detecting dissociable antibodies without the interference of the capture antibodies.

In another embodiment, the reagent-ligand complexes can be stabilized by covalent cross-linking which can be done at several steps, in particular, after the formation of capture reagent-ligand complexes; and/or after the formation of ligand-dissociable reagent complexes. There are hundreds of known cross-linkers and a variety of methods have been developed to use them to cross-link proteins (Wong, Shan S., Chemistry of protein conjugation and cross-linking. Boca Raton: CRC Press, 1993). A common cross-linking solution that can be used is a formaldehyde solution. A typical formaldehyde solution is 1% formaldehyde in phosphate-buffered saline. The concentration of formaldehyde can be varied and is applicable in many different buffer solutions. Another cross-linker is Glutaraldehyde. Another cross-linker is a homobifunctional N-hydroxysuccimide ester cross-linker, Bis (Sulfosuccinimidyl) suberate (BS, from Pierce, Rockford, Ill.).

In a preferred embodiment, a first antibody array (capture antibody array) is incubated with a protein sample that contains the target ligands (the proteins of interest); the ligands are captured and separated by respective capture antibodies immobilized on the first antibody array; removing non-binding proteins; the capture antibodies and ligands complexes are covalently cross-linked; aligning and contacting the ligands captured on the first antibody array with their respective dissociable antibodies on a second antibody array (dissociable antibody array), whereby the dissociable antibodies binds the ligands; removing the second antibody array from the first antibody array, whereby ligand-bound dissociable antibodies dissociate from the second array support and transferred to the first array support.

In another preferred embodiment, a first antibody array (capture antibody array) is incubated with a protein sample that contains the target ligands (the proteins of interest); the ligands are captured and separated by respective capture antibodies immobilized on the first antibody array; removing non-binding proteins; contact the ligands captured on the first antibody array with their respective dissociable antibodies on a second antibody array (dissociable antibody array), whereby the dissociable antibodies binds the ligands; remove the second antibody array from the first antibody array, whereby ligand-bound dissociable antibodies dissociate from the second array support and transferred to the first array support; covalently cross-link the ligand-dissociable antibody complexes.

In another preferred embodiment, a first antibody array (capture antibody array) is incubated with a protein sample that contains the target ligands (the proteins of interest); the ligands are captured and separated by respective capture antibodies immobilized on the first antibody array; removing non-binding proteins; covalently cross-link the capture antibodies and ligands complexes; contact the ligands captured on the first antibody array with their respective dissociable antibodies on a second antibody array (dissociable antibody array), whereby the dissociable antibodies binds the ligands; remove the second antibody array from the first antibody array, whereby ligand-bound dissociable antibodies dissociate from the second array support and are transferred to the first array support; covalently cross-linking the ligand-dissociable antibody complexes.

In another preferred embodiment, a ligand mixture (protein sample) is first incubated with a capture antibody array to allow antibodies to capture their respective interacting ligands on the array. After non-binding proteins are washed off, the capture antibody-ligands complexes are covalently cross-linked. The ligand-binding capture antibody array is then contacted with a dissociable antibody array; the two arrays are aligned so that the dissociable antibodies on the dissociable antibody array can bind to their respective interacting ligands captured on the capture antibody array. After incubation, the dissociable antibody array is removed from the capture antibody array; dissociable antibodies bound to the ligands dissociate from the dissociate antibody array and bind to the capture antibody array. The capture antibody array containing captured ligands and binding dissociable antibodies is then contacted with a third support under conditions so that the dissociable antibodies dissociate from the capture antibody array and bind to the third support and are transferred, immobilized on the third support. The transferred dissociable antibodies on the third support are then detected, e.g. with fluorescent secondary antibodies.

One motivation for cross-linking is to allow efficient transfer of dissociable reagents to a third support while minimizing the transfer of capture reagents. When no or minimal amount of capture reagents are transferred, the dissociable reagents transferred onto the third support can be easily detected; and when antibodies are used as capture and dissociable reagents, antibodies from the same species can be used in both dissociable antibody array and capture antibody array.

The cross-linking efficiency is high in the present method for several reasons. First, the proteins to be cross-linked interact with each other and thus are at close proximity.

Second, the proteins are at the interface of liquid and solid phase and are at high local concentration. Third, the cross-linking is devoid of interference by other irrelevant proteins.

There are advantages to use chemical cross-linking in the present method. For example, covalent cross-linking will simultaneously cross-link the proteins in a complex and stabilize the complex, thus increasing assay sensitivity. The method requires several steps of washes and incubations, which are needed before the production of the final detection signal. Although washing is necessary to avoid nonspecific protein binding, because protein-protein interactions are reversible, washing, especially a long extensive wash will inevitably disrupt some protein complexes. Even for strong interactions, such as some high-affinity antibody-antigen interactions with an association constant larger than $10^9$ $M^{-1}$, the half-life time for dissociation of antibody-antigen complexes is in the range of minutes (Sachs et al. Inactivation of staphylococcal nuclease by the binding of antibodies to a distinct antigenic determinant. Biochemistry Nov. 7, 1972; 11(23): 4268-73). The washing and incubation times are long enough to allow efficient dissociation between them. This is especially a problem for many less strong interactions. Therefore, if the dissociation of protein complexes were prevented by covalent cross-linking, the amount of protein complexes bound to the support would be increased, and consequently, the final signal would be enhanced.

The present invention provides a method to detect the interactions between two ligands. In an embodiment, an antibody against the first ligand is immobilized on a first support; then the first support is incubated with the complex of the first and the second ligands. After capturing the complex onto the first support, the first support is contacted with a second support on which a second antibody against the second ligand is immobilized. After the second antibody binds to the second ligand of the complex, the second support is separated from the first support. Then the second antibody dissociated from the second support and transferred to the first support is detected.

In another embodiment, capture antibody array and dissociable antibody array are used to detect a plurality of protein-protein interactions. In the method, antibodies against a first set of ligands are immobilized on a first support to make a capture antibody array; antibodies against a second set of ligands are immobilized on a second support to make a dissociable antibody array. The positions of the antibodies on the two arrays are arranged in such a way that when the two array supports are placed in contact, the antibodies against two interacting ligands are in close proximity. The capture antibody array is first incubated with a protein sample containing the protein complexes. After the capture antibodies bind and capture their antigens (therefore their interacting proteins) on the first support, non-binding proteins are washed off. Then the capture antibody array is aligned and contacted with the dissociable antibody array to allow dissociable antibodies to bind their respective antigens. After the dissociable antibody array is removed from the capture antibody array, the dissociable antibodies dissociated from the dissociable antibody array support and transferred onto the capture antibody array are detected.

In another embodiment, the capture antibody array is first incubated with a protein sample containing a first set of protein. After the capture antibodies bind and capture their antigens on the first support and non-binding proteins are washed off, the capture antibody array is incubated with a second set of protein to allow members of the second set of proteins to interact with the first set of proteins to form protein complexes. After washing off non-binding proteins, the capture antibody array is aligned and contacted with the dissociable antibody array to allow dissociable antibodies to bind their respective antigens. After the dissociable antibody array is removed from the capture antibody array, the dissociable antibodies dissociated from the dissociable antibody array support and transferred onto the capture antibody array are detected.

In another preferred method, cross-linking can be used in the procedures of detecting protein-protein interactions. In one preferred embodiment, cross-linking is performed after the capture antibody array binds the proteins/protein complexes. Cross-linking can also be performed after the formation of protein complexes, or after the binding between the protein/protein complexes and dissociable antibodies.

The present method can be used to detect protein post-translational modifications, such as protein phosphorylations. In one embodiment, antibodies against total proteins are immobilized on capture antibody arrays, and antibodies against phosphorylated tyrosine (e.g. mouse monoclonal antibodies 4G10 and PY20) are immobilized on the dissociable antibody array. In another embodiment, antibodies against total proteins are immobilized on capture antibody arrays, while antibodies specific to phosphor-proteins are immobilized on dissociable antibody arrays. In another embodiment, antibodies against phosphor-proteins are immobilized on capture antibody arrays, while antibodies against phosphorylated tyrosine (e.g. mouse monoclonal antibodies 4G10 and PY20) are immobilized on dissociable antibody arrays.

EXAMPLES

The following examples are for illustration only and in no way are intended to limit the present invention. Although the examples describe the use of reagent arrays comprising antibodies, similar usage for arrays of biological reagents other than antibodies are obvious to the people familiar with the arts. Such arrays of biological reagents include but are not limited to arrays of recombinant proteins, recombinant antibodies, single chain antibodies, nucleic acids, oligos, cDNA probes, carbohydrates, lipids, and small chemicals.

Example 1

Figure 2:
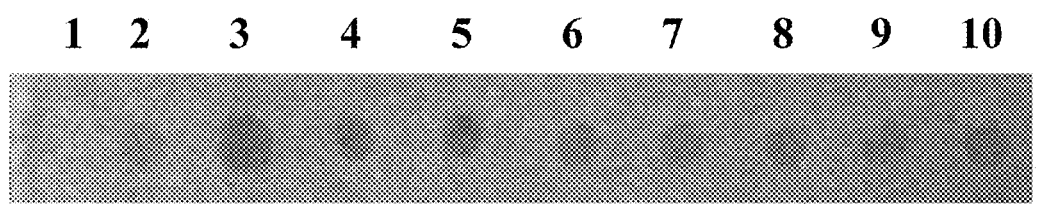
FIG. 2 shows an example of using a ligand array and a dissociable reagent array to detect multiple ligands in a biological sample.

In this example (FIG. 2) a cell lysate prepared from 293T human cells was immobilized at 10 spots on a nitrocellulose membrane to form a ligand array. About 2 micrograms of protein lysate was immobilized at each spot. 10 different rabbit polyclonal antibodies against 10 different cellular proteins were immobilized on a nylon membrane to form a dissociable antibody array. After blocking, the dissociable antibody array was laid on top of the ligand array to make contact. After 60 minutes incubation during which time antibodies bound to their respective antigens, the dissociable antibody array was removed from the ligand array. The ligand-bound antibodies stayed on the ligand array. Any non-specific binding antibodies were washed off; and the rabbit antibodies were detected with HRP-conjugated goat-anti-rabbit secondary antibodies. In this example, TMB was used as HRP substrate.

Example 2

In this example, unconjugated secondary antibodies were used to capture serum IgG while HRP-conjugated secondary antibodies were used as the detection/dissociable antibodies.

Figure 3:
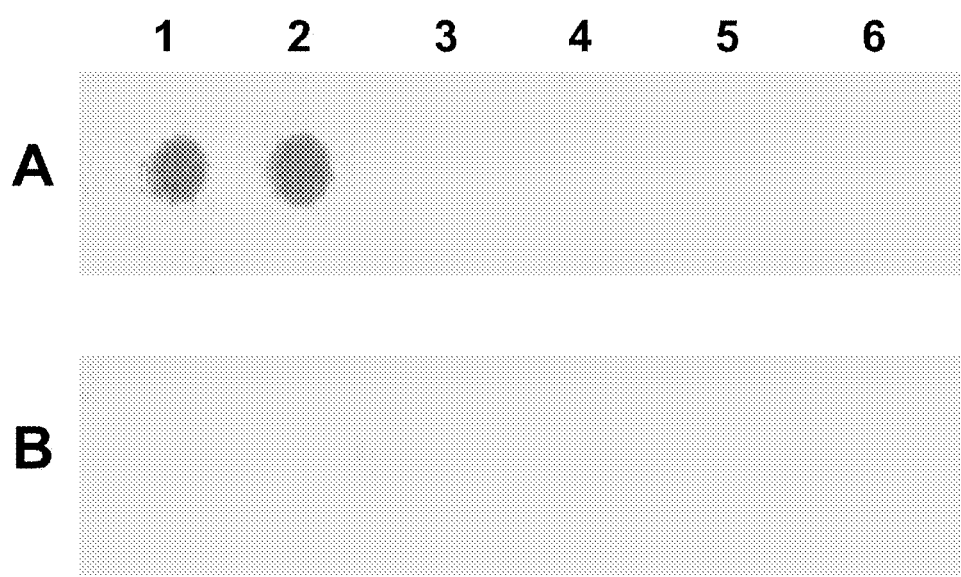
FIG. 3 shows an example of using a capture antibody array and a dissociable antibody array to detect mouse antibodies in a protein sample.

Goat-anti-mouse and goat-anti-rabbit IgG($F_c$) antibodies were spotted on a silane-coated glass slide and covalently immobilized on it to produce the capture antibody microarray. To make a dissociable antibody microarray, HRP-conjugated goat-anti-mouse or goat-anti-rabbit IgG [F(ab')$_2$] antibodies were spotted on a nylon membrane with a glass slide as backing. About 80 nl antibody solutions were deposited at each spot 2 mm apart; each antibody was spotted in duplicate. The capture and detection antibodies recognize different epitopes ($F_c$ and F(ab')$_2$, respectively) of the IgG ligand. Mouse serum (1:1000 dilution) was used as target ligand. HRP substrate Tetramethylbenzidine Dihydrochloride was used to visualize the bound HRP-conjugated detection antibody. As shown in FIG. 3A, signals were detected at the positions of matched antibody pairs (1 and 2, goat-anti-mouse antibodies on both capture and dissociable arrays) but not at the positions of mismatched antibody pairs (3 and 4, goat-anti-mouse antibody on capture array and goat-anti-rabbit on dissociable array; 5 and 6, goat-anti-rabbit antibody on capture array while goat-anti-mouse on dissociable array).

In the control experiments (FIG. 3B), the same capture and dissociable antibody arrays were used. Rabbit serum (1:1000 dilution) instead of mouse serum was used. As expected, no signal was detected at any positions because there were no matching goat-anti-rabbit antibodies at any position.

Example 3

In this example, two antibody arrays were prepared and used to detect proteins according to the method disclosed here. Antibodies from commercial sources (about 0.2 µg/µl) were arrayed on membranes using a robotic arrayer to make both capture and dissociable antibody arrays. Nitrocelluose membrane was used as capture antibody array support; and nylon membrane was used as dissociable antibody array support. All antibodies on the capture antibody array are from rabbit; and all antibodies on the dissociable antibody array are from mouse. Decreasing amounts of antibodies were immobilized in each row on the capture antibody arrays. Rows 1 and 3 are antibodies against Connexin43 protein, and rows 2 and 4 are antibodies against GST protein. Same amount of antibodies (40 ng) were immobilized in each row on dissociable antibody array. Antibodies were immobilized by non-covalent bonds between nylon/nitrocelluose membranes and the antibodies. Antibody arrays were either used immediately or stored at 4° C. for less than 48 hrs before use.

Figure 4:
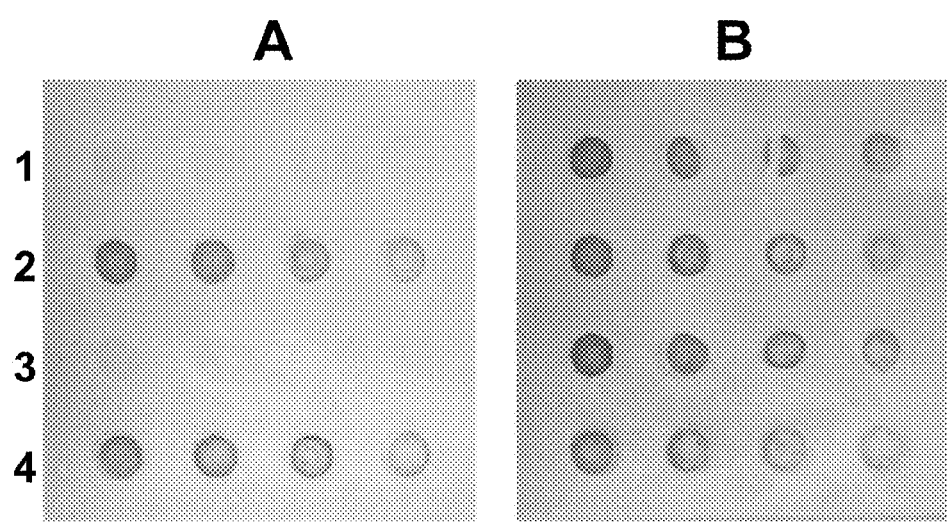
FIG. 4 shows an example of using two antibody arrays to detect two proteins in bacterial lysates.

A capture antibody array was first blocked in 1% BSA solution for 1 hr, and then incubated with a lysate containing GST (FIG. 4A) or a lysate containing both GST and Connexin43 (FIG. 4B). During the incubation the antibodies bound their respective antigens. Afterward, non-binding proteins were washed off with phosphate-buffered saline.

1% glutaraldehyde in phosphate-buffered saline was used to cross-link the antibodies and binding antigens.

A dissociable antibody array was then overlaid on top of the capture antibody array. The two arrays were aligned so that each of the antibodies on the dissociable antibody array would make contact with its intended targets captured on the capture antibody array. During 1-hour incubation, the dissociable antibodies bound to their respective ligands. After incubation, when the dissociable antibody array was removed from the capture antibody array, the dissociable antibodies that bound to the targets dissociated from the dissociable antibody array and transferred to the capture antibody array. After a few washing with PBS, alkaline phosphatase-labeled secondary antibodies were added for half an hour. After wash, the signal was visualized by color reaction with 5-bromo-4-chloro-indolyl-phosphatase (BCIP) and nitroblue tetrazolium (NBT) as substrates. The enzymatic reaction was stopped by washing off substrates with PBS and the image was obtained by scanning with a flat-bed scanner.

In the assay with lysate containing GST protein, signals were detected at positions immobilized with GST antibodies (FIG. 4A, rows 2 and 4); while in the assay with lysate containing both GST and Connexin43 proteins (FIG. 4B), signals were detected at all positions, immobilized with either GST antibodies (rows 2 and 4) or connextin43 antibodies (rows 1 and 3).

Example 4

Figure 5:
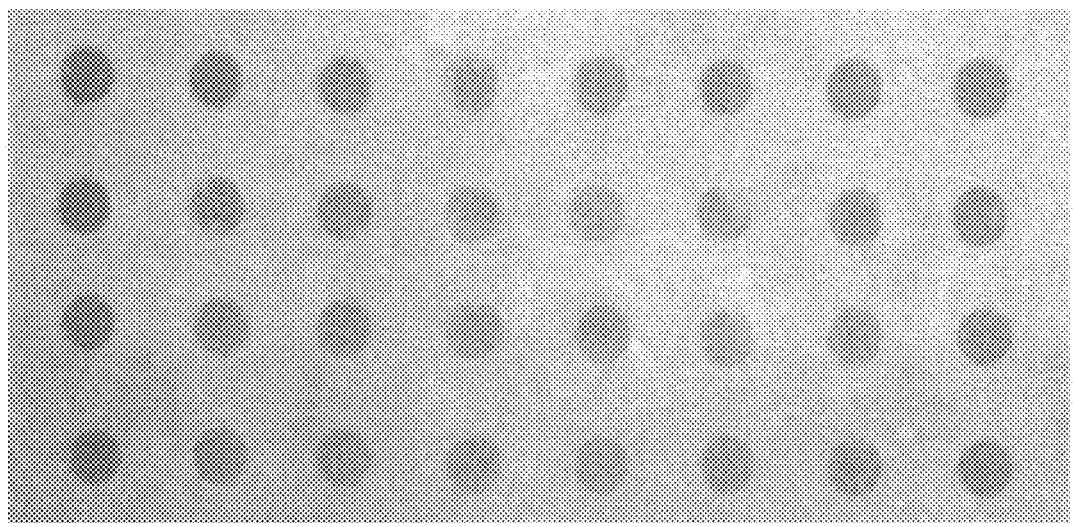
FIG. 5 shows an example of using a preferred method to detect proteins.

In this example, a capture antibody array was made by immobilizing a rabbit-anti-mouse antibody at 32 spots on a glass slide support. A dissociable antibody array was made by immobilizing a HRP-conjugated goat-anti-mouse antibody at 32 spots on a nylon membrane. The antibodies were immobilized on the capture antibody array and dissociable antibody array at pre-determined position so that when the two arrays make contacts, the antibody pair will be in close proximity. The capture antibody array was first incubated with about 20 nanograms of mouse antibody. During the incubation, mouse antibody was captured by the antibodies immobilized on the capture array. PBS solution was used to rinse off any non-binding antibodies. The complexes formed between rabbit-anti-mouse antibodies and mouse antibodies were further stabilized by cross-linking with 1% glutaraldehyde. Then the dissociable antibody array was placed over the capture antibody array in such a way that, each of the HRP-conjugated goat-anti-mouse dissociable antibodies made contact with mouse antibody captured on the capture antibody array. After binding, the dissociable array was removed from the capture antibody array support. Because some goat-anti-mouse antibodies bound their antigens, they dissociated from the dissociable array support and bound to the capture array support. Afterwards, a third membrane support (a nitrocellulose membrane) was place on the capture antibody array to allow the dissociable antibodies to dissociate from the capture antibody array and transferred and immobilized on the third support. After adding HRP substrate, chemiluminescence signal was capture by a cooled CCD camera (FIG. 5).

Although specific features of the invention are shown in some drawings and examples, this is for convenience only as some features may be combined with any or all of the other features in accordance with the invention. Other embodiments and modifications will occur to those skilled in the art and are within the following claims:

What is claimed is:

1. A method for detecting two or more ligands, comprising the steps of:
   providing a ligand array, comprising a first support on which two or more ligands are immobilized, each at one or more predefined positions;
   providing a dissociable reagent array, comprising a second support on which two or more dissociable reagents are immobilized, each at one or more predefined positions;
   aligning and contacting the ligand array with the dissociable reagent array whereby the dissociable reagents bind to the ligands on the first support;

separating the second support from the first support; and detecting the dissociable reagents bound to the ligands on the first support, whereby one or more of the ligands are detected.

2. The method of claim 1, wherein said dissociable reagents are antibodies.

3. The method of claim 1, wherein said second support comprises materials selected from the group consisting of nylon and its derivatives.

4. The method of claim 1, wherein 5 to 2000 different kinds of dissociable reagents are each immobilized at one or more predetermined positions on said second support.

5. A method for detecting one or more ligands, comprising the steps of:

provide a capture reagent array, comprising a first support on which one or more capture reagents are immobilized, each at one or more predefined positions;

contacting the capture reagent array with the ligands, whereby the ligands are captured and separated on the first support;

providing a dissociable reagent array, comprising a second support on which one or more dissociable reagents are immobilized, each at one or more predefined positions;

aligning and contacting the capture reagent array with the dissociable reagent array whereby the dissociable reagents bind to one or more of the ligands captured on the first support;

separating the second support from the first support, whereby the dissociable reagents are transferred from the second support to the first support.

6. The method of claim 5, wherein said capture or dissociable reagents are selected from the group consisting of antibodies, recombinant proteins, peptides, DNA, RNA, oligo nucleotides, carbohydrates, and small chemicals.

7. The method of claim 6, wherein said capture or dissociable reagents are antibodies.

8. The method of claim 7, wherein one or more of said capture or dissociable reagents are antibodies specific for posttranslationally modified proteins.

9. The method of claim 7, wherein one or more of said capture or dissociable reagents are antibodies specific for phosphorylated proteins.

10. The method of claim 5, wherein 5 to 2,000 different kinds of dissociable reagents are each immobilized at one or more predetermined positions on said second support.

11. The method of claim 10, wherein 20 to 1,000 different kinds of dissociable reagents are each immobilized at one or more predetermined positions on said second support.

12. The method of claim 5, wherein said first support or said second support comprises materials selected from the group consisting of nitrocellulose, nylon, polyvinylidene difluordie, glass, or plastic, and their derivatives.

13. The method of claim 12, wherein said second support comprises materials selected from the group consisting of nylon and its derivatives.

14. The method of claim 5, further comprising the step of covalently cross-linking one or more of said capture reagents with one or more of said ligands before contacting said dissociable reagent array and said capture reagent array.

15. The method of claim 14, wherein said step of covalent cross-linking uses one or more aldehydes.

16. The method of claim 15, wherein one or more of said aldehydes are selected from the group consisting of formaldehyde and glutaraldehyde.

17. The method of claim 7, wherein all capture antibodies on the capture antibody array are rabbit antibodies; and all dissociable antibodies on the dissociable antibody array are mouse antibodies.

18. The method of claim 7, wherein all capture antibodies on the capture antibody array are mouse antibodies; and all dissociable antibodies on the dissociable antibody array are rabbit antibodies.

19. The method of claim 5, further comprising the steps of:

contacting the first support with a third support;

transferring the dissociable reagents from the first support to the third support; and detecting the dissociable reagents transferred to the third support.

20. The method of claim 19, further comprising the step of covalently cross-linking one or more of the capture reagents with one or more of the ligands before aligning and contacting the capture reagent array with the dissociable reagent array.

* * * * *